United States Patent [19]

Mulchin

[11] Patent Number: 4,671,795
[45] Date of Patent: Jun. 9, 1987

[54] PERMANENT/RETRIEVABLE URETERAL CATHETER

[76] Inventor: William L. Mulchin, 10 Medical Pkwy., Suite 207, Professional Plaza 3, Dallas, Tex. 75234

[21] Appl. No.: 672,933

[22] Filed: Nov. 19, 1984

[51] Int. Cl.⁴ .......................................... A61M 25/00
[52] U.S. Cl. ........................................ 604/281; 604/8; 604/264
[58] Field of Search ............... 604/281, 8, 264, 270, 604/271, 280, 285, 282

[56] References Cited

U.S. PATENT DOCUMENTS

| | | | |
|---|---|---|---|
| 2,212,334 | 8/1940 | Wallerich | 604/280 |
| 2,508,690 | 5/1950 | Schmerl | 604/265 |
| 2,707,958 | 5/1955 | Davis | 604/280 |
| 3,421,499 | 1/1969 | Bray et al. | 604/270 |
| 3,920,023 | 11/1975 | Dye et al. | 604/281 |
| 3,948,272 | 4/1976 | Guibor | 604/264 |
| 3,995,642 | 12/1976 | Adair | 604/8 |
| 4,117,836 | 10/1978 | Erikson | 604/281 |
| 4,279,252 | 6/1981 | Martin | 604/280 |
| 4,286,596 | 9/1981 | Rubinstein | 604/285 |
| 4,471,782 | 9/1984 | Sheffield | 604/104 |
| 4,531,933 | 7/1985 | Norton et al. | 604/281 |

FOREIGN PATENT DOCUMENTS

A006922  4/1907  France ................ 604/264

Primary Examiner—C. Fred Rosenbaum
Assistant Examiner—Mark Rooney
Attorney, Agent, or Firm—Jerry R. Selinger; Jerry W. Mills

[57] ABSTRACT

An improved universally-sized permanent/retrievable ureteral catheter adapted to be cystoscopically inserted and positioned within a patient and adapted to be removed from the patient without the use of a cytoscopic procedure is disclosed. It includes an elongated, relatively flexible, generally cylindrical member defining a plurality of apertures therein for avoiding catheter blockage during use and having a proximal end defining a single coil, a relatively straight, long intermediate section and a distal end. The coiled proximal end is made of an inert material and is adapted to be straightened so that the catheter may be cystoscopically inserted and positioned within a patient. The coiled proximal end reforms upon insertion and prevents the member from migrating. The elongated, relatively flexible, generally cylindrical member is adapted to be cut along its distal end to fit the needs of a specific patient. A suture having a free portion and an affixed portion is connected along the intermediate section of the elongated, relatively flexible, generally cylindrical member by means of the affixed portion. The free portion is adapted to be positioned outside a patient when the catheter is inserted into position and when it is desired later to remove the catheter. The catheter may be removed by pulling on the suture without the use of a cytoscopic procedure.

4 Claims, 2 Drawing Figures

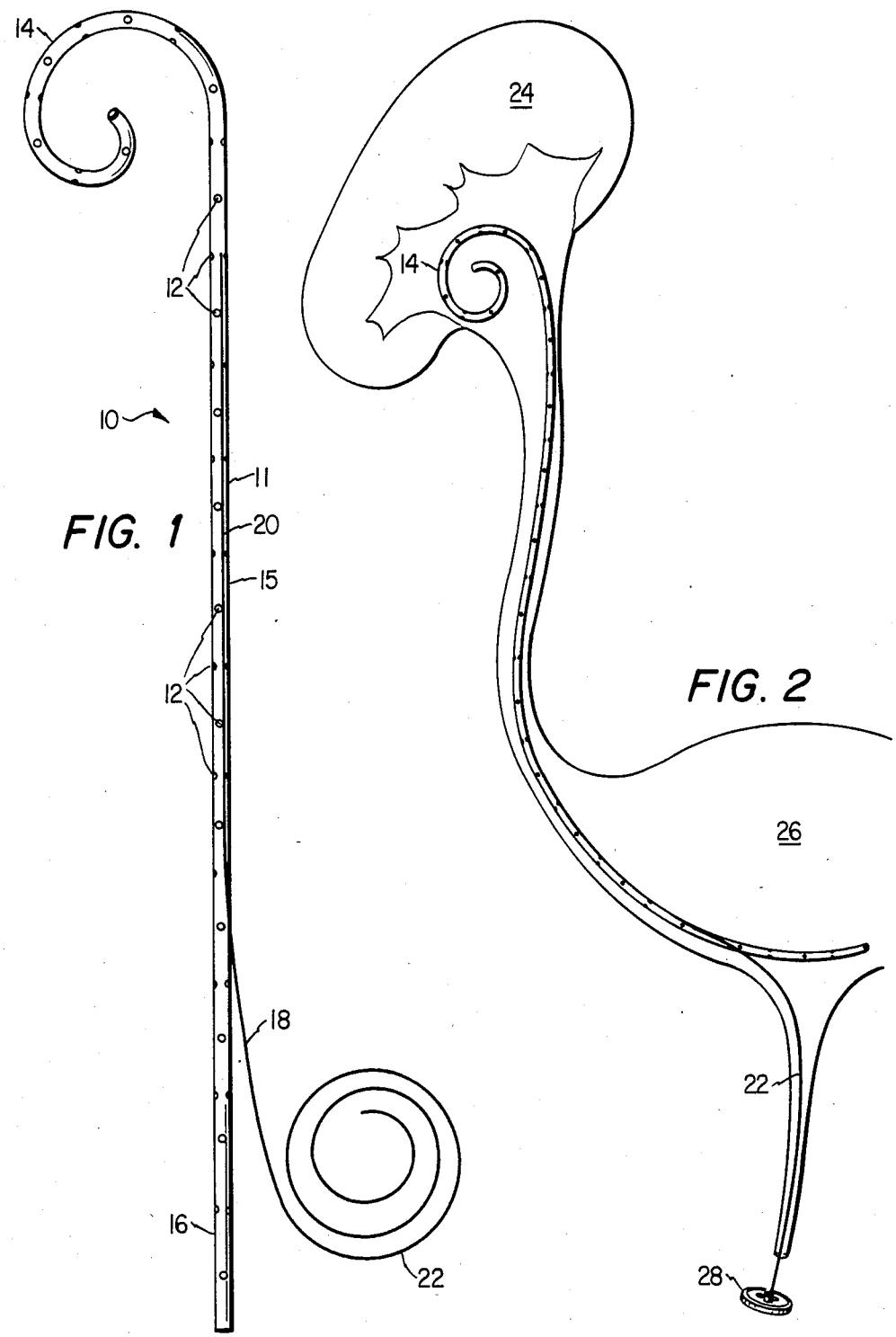

4,671,795

PERMANENT/RETRIEVABLE URETERAL CATHETER

TECHNICAL FIELD OF THE INVENTION

The present invention relates to ureteral catheters. More particularly, it relates to an improved universally-sized, permanent/retrievable ureteral catheter inserted by cystoscopic procedure which once in place resists migration, and which can be removed from the patient without the use of or need for a second cystocopic procedure.

BACKGROUND OF THE INVENTION

In endoscopic surgery, a ureterscope is inserted into the intramural ureter. In order to so insert the ureterscope, that portion of the ureter must be dilated to at least a 12F. This results in severe enough swelling that after the procedure, the lumen may swell shut, causing colic. Ureteral catheters or drainage tubes are well known. However, the prior art ureteral catheters suffer from several common deficiencies. First, after a catheter is cystoscopically inserted, a second operative procedure (resulting in both discomfort and expense to the patient) is necessary. Second, the catheters often do not remain in place. Third, the catheters are of specific, noninterchangeable sizes. Consequently, hospitals are required to maintain a supply of variously-sized catheters.

Examples of United States patents which pertain to ureteral catheters that reflect one or more of these deficiencies include U.S. Pat. No. 2,707,958; 3,995,642 and 4,307,723. Each of these patents contemplates the use of a cystoscopic procedure both to insert and to remove the respective devices. This is disclosed in the U.S. Pat. No. 2,707,958 at column 3, lines 2–3. It is disclosed in U.S. Pat. No. 3,995,642 in column 2, lines 49–53. Finally, U.S. Pat. No. 4,307,723 exhibits the same contemplation at column 4, lines 55–60.

There are also three sources of catheters currently on the market which are known to be used in procedures of this type. One such product is manufactured by Vance's, P.O. Box 227, Spencer, Ind. 47460, and bears identification no. V90183. This ureteral pigtail stint suffers from the disadvantage that it is too stiff so that it irritates the bladder excessively. In addition, it comes in pre-cut multiple catheter sizes, and a second operative procedure is required to remove the device. The second product is manufactured by the Bard Urological Division of C. R. Bard, Inc. in Murray Hill, N.J. 07974, and bears identification number 02L34008. This device has multiple coils and suffers from disadvantages in that these coils can rewind in the bladder and pull the coil out of the kidney. It, too, requires a cystoscopy for removal. The third such product is made by Medical Engineering Corp., 3037 Mt. Pleasant Street, Russine, Wis. 53404. It also comes in multiple sizes and requires a second operative procedure for removal.

SUMMARY OF THE INVENTION

It is the general object of the present invention to disclose a ureteral catheter that can be used to prevent closing of the ureteral after the intramural ureter has been dilated in order to permit the insertion of a rigid or flexible ureterscope into the ureter. It is still a further object of the present invention to provide a ureteral catheter which is universally-sized, which will not migrate once it has been placed inside a patient and which may be removed without the need for a second operative procedure.

The subject invention comprises an elongated, flexible, cylindrical member which has proximal and distal ends and defines a longitudinal axis. The elongated, flexible, cylindrical member is of substantially uniform outside diameter throughout the entire length thereof and defines a plurality of apertures therein. The proximal end of the elongated, flexible, cylindrical member is set in the form of a curl and is of denser material than the remainder of the elongated, flexible, cylindrical member in order to keep the curl shape. The overall length of the catheter is approximately 34 centimeters, with the proximal end and the distal end each being about four centimeters in length. The catheter can be cut at the distal end to any appropriate length. A 3-0 monofilament synthetic suture with radio opaque characteristics is connected to the elongated, flexible, cylindrical member along a substantial portion of the longitudinal axis thereof. It separates from the member about four centimeters from the end of the distal end and is adapted to extend therebeyond. The catheter is inserted by a cystoscopic procedure over a wire guide which causes the entire catheter to be straightened out. Once the catheter is in place, the wire guide is removed and the proximal end returns to its coil shape to hold the catheter in position. The suture extends out of the urethra and is tied to a button to prevent upward migration. The catheter may be removed by simply pulling on the suture. The needed catheter length can be determined prior to insertion and the distal end cut to the proper length.

BRIEF DESCRIPTION OF THE DRAWING

FIG. 1 is a side elevation of the subject of the invention; and

FIG. 2 diagramatically illustrates the invention when disposed in a ureter with its end communicating a kidney and bladder.

DETAILED DESCRIPTION OF PREFERRED EMBODIMENT

Referring now to FIG. 1 of the drawings, the ureteral catheter 10 of the subject invention comprises a flexible plastic tube 11 having apertures 12 along the length thereof. Apertures 12 are provided along the length of tube 11 for drainage and circulation. For instance, if a clot forms within tube 11, drainage can continue to occur by having the draining fluid exit from aperture 12 and travel along the outside of tube 11, either to the terminus thereof or until it re-enters tube 11 through another aperture 12. The tube 11 defines a proximal end 14 which is set in the form of a curl, an intermediate portion 15 and a distal end 16. In the preferred embodiment, proximal end 14 is sealed and distal end 16 is open, although it can be manufactured with a sealed end that is opened during surgery. A monofilament synthetic suture 18 defines a first portion 20 which is connected to tube 11 either by being embedded in the wall of tube 11 or by being adhered thereto by any conventional means and a second, free portion 22.

Tube 11 is made of inert material, such as silicone. The overall length of tube 11 is about 34 centimeters, and its calibre (outside diameter) is in the range of 6–7 French. The calibre of tube 11 should be substantially uniform, and the lumen (inside diameter) should also be substantially constant throughout. The proximal end 14 is approximately four centimenters in length and is constructed of a denser inert polymer than is the remaining portion of tube 1, so that in its free state end 14 will maintain the curled shape after insertion into a kidney 24 in the fashion described below. Distal end 16 also is approximately four centimeters in length and is adapted to be shortened by removing a portion of the end 16 to tailor the overall length of catheter 10 to the needs of any specific patient.

Suture 18 is preferably a 3-0 monofilament synthetic suture with opaque characteristics to x-rays. Such characteristics can be imparted to the suture 18 by impregnating it with a radio-opaque solution. The suture 18 is attached to tube 11 along intermediate portion 15. It can be, but does not have to be, attached to the proximal end 14 of tube 11, but it should not be attached to distal end 16 because that is the segment which is cut to tailor the catheter 10 to the appropriate length. Free portion 22 of suture 18 is not attached to tube 11 and is adapted to be used as described hereinbelow. The suture 18 may be affixed longitudinally either to the inside or outside of tube 11, although if it is mounted inside, care needs to be taken to ensure it will not be knocked loose during the insertion process. If the catheter 10 is to be permanently inserted, free portion 22 may be removed during surgery.

Referring now to FIG. 2, the catheter 10 is shown in its operative position. Catheter 10 extends from kidney 24 into bladder 26. Proximal end 14 is placed within kidney 24. The curl of proximal end 14 ensures that the catheter 10 will not get milked out of kidney 24 by peristalsis. The free portion 22 of suture 18 is adapted to extend outwardly through the urethra (not shown) and may be secured to a button 28 to ensure that the catheter 10 does not migrate proximally and to allow easy removal.

The catheter 10 of the subject invention is utilized in the following fashion in connection with cystoscopic insertion. A wire stylet (not shown) is inserted through the distal end 16 and passed through the full length of tube 11 to straighten the curl of proximal end 14. The straightened catheter 10 (which already has been cut to the desired length) is then inserted cystoscopically between a patient's kidney 24 and bladder 26 as shown in FIG. 2. Once the stylet is withdrawn, the curl at the proximal end 14 reforms to prevent migration of the catheter 10 out of the kidney 24. The free portion 22 of the suture 18 is passed through the patient's urethra and is tied in place outside of the patient by means of button 28. Since the suture 18 is preferably radio-opaque, it is possible to ascertain the position of the catheter 10, after the wire guide has been removed.

The tip of the proximal end can be trimmed so that the inner lumen is seen and the catheter can be passed over the guide wire, which may be positioned through the ureteroscope.

When it is time to remove the catheter 10 of the subject invention, it may simply be removed by pulling on the suture 18.

In the preferred embodiment described and shown in the drawings, the proximal end 14 of the catheter 10 is in the form of a curl. However, it is to be understood that the term "curl" is intended to include other functionally equivalent shapes which prevent migration and do not increase the effective outer diameter of the device or complicate its method of introduction. It will be readily apparent to those skilled in the art that a number of other modifications and changes can be made without departing from the spirit of the invention. Therefore, it is to be understood that the scope of the invention is not to be measured by the description, but only by the claims that follow.

What is claimed is:

1. An improved universally-sized permanent/retrievable ureteral catheter adapted to be inserted and positioned within a patient and adapted to be removed from the patient without the use of a second operative procedure, comprising:

an elongated, relatively flexible, generally cylindrical member containing a plurality of apertures along a substantial portion thereof for avoiding catheter blockage during use and having a proximal end defining a single coil, a relatively straight, long intermediate section and a distal end, said proximal end being made of an inert material and adapted to be straightened so that the catheter may be inserted and positioned within a patient whereupon the coiled proximal end reforms in the renal pelvis and proximal ureter and prevents the member from migrating; and a suture having a free portion and an affixed portion, said affixed portion being connected substantially along the intermediate section of said elongated, relatively flexible, generally cylindrical member and remote from the distal end thereof, said free portion adapted to be positioned outside a patient for subsequent removal when said catheter is inserted into position, whereby said catheter is prevented from migrating into the kidney and may be removed from the patient along the natural channels by pulling on the suture without the use of a second operative procedure; and whereby the elongated, relatively flexible, generally cylindrical member can be cut along its distal end to fit the needs of a specific patient without also severing the affixed portion of the suture from the elongated, relatively flexible, generally cylindrical member.

2. The improved device of claim 1 wherein said proximal end is of denser material than said intermediate section of said elongated, relatively flexible, generally cylindrical member to maintain the coil within the kidney upon insertion.

3. The improved device of claim 2 wherein said suture is comprised of a 3-0 monofilament having radio-opaque characteristics and wherein said catheter has an initial overall length of about 34 centimeters with each of said distal end and said proximal end being about four centimeters in length.

4. The improved device of claim 3 wherein said affixed portion of said suture is connected substantially along the intermediate section and the proximal end of said elongated, relatively flexible, generally cylindrical member.

* * * * *